(12) United States Patent
Yagc I Acar et al.

(10) Patent No.: US 10,138,419 B2
(45) Date of Patent: Nov. 27, 2018

(54) NEAR-IR EMITTING CATIONIC SILVER CHALCOGENIDE QUANTUM DOTS

(71) Applicant: KOÇÜNIVERSITESI, Istanbul (TR)

(72) Inventors: Havva Yagc I Acar, Istanbul (TR); Fatma Demir, Istanbul (TR)

(73) Assignee: KOÇ ÜNIVERSITESI, Istanbul (TR)

( * ) Notice: Subject to any disclaimer, the term of this patent is extended or adjusted under 35 U.S.C. 154(b) by 0 days.

(21) Appl. No.: 15/323,396

(22) PCT Filed: Aug. 13, 2014

(86) PCT No.: PCT/TR2014/000317
§ 371 (c)(1),
(2) Date: Dec. 30, 2016

(87) PCT Pub. No.: WO2016/024924
PCT Pub. Date: Feb. 18, 2016

(65) Prior Publication Data
US 2017/0152435 A1    Jun. 1, 2017

(51) Int. Cl.
*A61K 9/00*    (2006.01)
*C09K 11/02*    (2006.01)
(Continued)

(52) U.S. Cl.
CPC ........ *C09K 11/025* (2013.01); *A61K 49/0067* (2013.01); *C01B 19/007* (2013.01); *C01G 5/00* (2013.01); *C09D 179/02* (2013.01); *C09K 11/02* (2013.01); *C09K 11/582* (2013.01); *C09K 11/881* (2013.01); *G01N 33/588* (2013.01); *B82Y 5/00* (2013.01); *B82Y 20/00* (2013.01);
(Continued)

(58) Field of Classification Search
CPC .................................................. C09K 11/025
See application file for complete search history.

(56) References Cited

U.S. PATENT DOCUMENTS

2004/0072937 A1   4/2004   Tomalia et al.
2014/0209393 A1*   7/2014   Jamison .................. E21B 21/00
                                                                        175/217

FOREIGN PATENT DOCUMENTS

EP          1868938 A2    12/2007
EP          2716733 A1    4/2014
(Continued)

OTHER PUBLICATIONS

Triulzi, Immunoassay based on the antibody-conjugated PAMAM-dendrimer-gold quantum dot complex, Chem. Comm., 2006, 5068-5070.*
(Continued)

*Primary Examiner* — Paul W Dickinson
(74) *Attorney, Agent, or Firm* — Gokalp Bayramoglu

(57) ABSTRACT

A novel near-IR emitting cationic silver chalcogenide quantum dot with a mixed coating wherein the coating comprises of at least 2 different types of materials and is capable of luminescence at the desired near IR bandwidth at wavelengths of 800-850 nm. The quantum dot is fabricated via an advantageous single-step, homogeneous, aqueous method at a low temperature resulting a near IR emitting semiconductor quantum dot with high Quantum Yield, high transfection with low toxicity. The quantum dots may be used in medical imaging, tumor detection, drug delivery and labeling as well as in quantum dot sensitized solar cells.

29 Claims, 4 Drawing Sheets

(51) Int. Cl.
- C09K 11/58 (2006.01)
- C09K 11/88 (2006.01)
- A61K 49/00 (2006.01)
- C01G 5/00 (2006.01)
- C01B 19/00 (2006.01)
- C09D 179/02 (2006.01)
- G01N 33/58 (2006.01)
- B82Y 5/00 (2011.01)
- B82Y 20/00 (2011.01)
- B82Y 40/00 (2011.01)

(52) U.S. Cl.
CPC ........... B82Y 40/00 (2013.01); C01P 2004/04 (2013.01); C01P 2004/64 (2013.01); Y10S 977/774 (2013.01); Y10S 977/892 (2013.01); Y10S 977/896 (2013.01); Y10S 977/906 (2013.01); Y10S 977/927 (2013.01)

(56) References Cited

FOREIGN PATENT DOCUMENTS

| WO | WO2004020969 A2 | 3/2004 |
| WO | WO2005093422 A2 | 10/2005 |
| WO | WO2012163078 A1 | 12/2012 |

OTHER PUBLICATIONS

L Shen: "Biocompatible Polymer/Quantum Dots Hybrid Materials: Current Status and Future Developments", Journal of Functional Biomaterials, No. 2, Dec. 2, 2011(Dec. 2, 2011), pp. 355-372, XP002737721, DOI: 10.3390/jfb2040355 p. 362; figures 2,3,5.

X Zhang; Y Gu, H Chen: "Synthesis of biocompatible near infrared fluorescence Ag2S quantum dot and its application in bioimaging", Journal of Innovative Optical Health Sciences, vol. 7, No. 3, 1350059, Nov. 28, 2013(Nov. 28, 2013), XP002737722, DOI: 10.1142/S1793545813500594 Introduction and experimenetal.

Rijun Gui et al: "Water-soluble multidentate polymers compactly coating Ag2S quantum dots with minimized hydrodynamic size and bright emission tunable from red to second near-infrared region", Nanoscale, vol. 6, No. 10, Jan. 1, 2014(Jan. 1, 2014), p. 5467, XP055178590, ISSN:2040-3364, DOI:10.1039/c4nr00282b experimental, results and discussion.

Nan Chen et al:"The cytotoxicity of cadmium-based quantum dots", Biomaterials,33 (2012) pp. 1238-1244,doi:10.1016/j.biomaterials.2011.10.070.

G.A. Martínez-Castanon et al:"Characterization of silver sulfide nanoparticles synthesized by a simple precipitation method", Materials Letters 59 (2005) pp. 529-534, doi:10.1016/j.matlet.2004.10.043.

Du Y et al:"Near-Infrared Photoluminescent Ag2S Quantum Dots from a Single Source Precursor", JACS, vol. 132, No. 5,Jan. 15, 2010(Jan. 15, 2010), p. 1470-1471, DOI:10.1021/ja909490r.

Jiang P et al:"Emission-Tunable Near-Infrared Ag2S Quantum Dots", Chemistry of Materials, 2011;24: 3-5.

Sahu A. et al:"Facile Synthesis of Silver Chalcogenide (Ag2E; E=Se, S, Te) Semiconductor Nanocrystals", JACS,2011; 133: 6509-6512.

Yarema M et al:"Infrared Emitting and Photoconducting Colloidal Silver Chalcogenide Nanocrystal Quantum Dots from a Silylamide-Promoted Synthesis", ACS Nano, vol. 5, No. 5, 2011, pp. 3758-3765, DOI:10.1021/nn2001118.

J. Mater.et al:"Development of highly luminescent and cytocompatible near-IR-emitting aqueous Ag2S quantum dots", Journal of Materials Chemistry, 2012, 22, pp. 14674-14681, DOI: 10.1039/c2jm31959d.

Yan et al:"One-pot synthesis of water-dispersible Ag2S quantum dots with bright fluorescent emission in the second near-infrared window", Nanotechnology, 2013, 24, 055706, DOI:10.1088/0957-4484/24/5/055706.

Tan et al:"Synthesis of near-Infrared Quantum Dots in Cultured Cancer Cells",ACS Applied Materials & Interfaces,2013,6, pp. 18-23.

Won et al:"Imaging Depths of Near-Infrared Quantum Dots in First and Second Optical Windows",Molecular Imaging,vol. 11, No. 4 (Jul.-Aug. 2012): pp. 338-352, DOI 10.2310/7290.2011.00057.

* cited by examiner

NEAR-IR EMITTING CATIONIC SILVER CHALCOGENIDE QUANTUM DOTS

CROSS REFERENCE TO RELATED APPLICATIONS

This application is the national phase entry of International Application No. PCT/TR2014/000317, filed on Aug. 13, 2014, the entire contents of which are incorporated herein by reference.

FIELD OF INVENTION

The present invention is related to novel Near Infra Red (NIR) emitting cationic silver chalcogenide quantum dots with mixed coatings (FIG. 1) which are capable of narrow bandwidth NIR emissions with high quantum yields, high transfection efficiency and to cytotoxicity and the method of synthesis and the uses thereof.

BACKGROUND OF THE INVENTION

Quantum Dots (QD) are quantum confined semiconductor nanoparticles. QDs exhibit luminescence properties when excited at a suitable wavelength and exhibit, in part, a size dependent emission wavelength as it is known in the art. Quantum Dots offer many advantages over traditional organic fluorescent dyes due to their unique properties such as 1) continuous absorbance and narrow emission bandwidth 2) ability to excite Quantum Dots emitting at different wavelengths simultaneously at a single excitation wavelength 3) ability to tune emission wavelength by the size of the semiconductor crystal and/or by the composition of the Quantum Dot in a broad spectral region 4) large absorbance cross-section and high molar absorptivity 5) long luminescent lifetime which allow longer analysis/detection time. Also, surface of QDs can be functionalized as hydrophilic or hydrophobic for suspension in aqueous or organic (oily) medium. Therefore, lately, quantum dots (QDs) are replacing organic fluorophores.

In the field of biotechnology and medicine, spectral window where quantum dots are excited and emitting is very critical. Best spectral window is usually accepted as 700-900 nm where the natural tissue has no or minimal absorbance and luminescence. This not only provides a better contrast in the imaging but also provides possibility for photons to penetrate or travel several centimeters in tissue, therefore allow relatively deeper tissue imaging.

An important handicap of Quantum Dots is the toxicity problem. Most common structures such as cadmium chalcogenides usually are excited at UV-range and emit in the visible region which is not a desired spectral window and these quantum dots are toxic. There are different approaches to solve these problems: One of which is the surface modification of the quantum dots with biocompatible materials. For example, a carbohydrate encapsulated quantum dot was disclosed in a patent application, WO 2005/093422 A2, in 2005. Another example to biological coatings is reported in a patent application, EP 1 868 938 A2, wherein Glutathione encapsulated CdTe quantum dot is synthesized. Similarly, several core/shell or core/shell/shell type structures wherein the shell is again a chalcogenide with usually a broader band gap and preferentially free of Cd were also reported. (N. Chen et al. Biomaterials 33 (2012), 1238-1244)

Another limitation in this area is the challenge of synthesizing a good quality quantum dot. Good quality means, relatively monodisperse, with narrow omission bandwidth and having high quantum yield. Generally speaking, good quality quantum dots are prepared in organic solvents, from relatively toxic starting materials at high temperatures (200-400° C.). Therefore the resulting hydrophobic particles turn out to be unsuitable for biomedical applications and the surfaces of such QDs are modified with organic molecules which will allow suspension of these particles in aqueous medium. However, this process is time consuming, expensive and usually causes loss in luminescence properties and a shift in the luminescence wavelength and may also result in aggregation of particles. Aqueous synthesis of quantum dots is an alternative for the organic synthesis, but this approach most of the time results in quantum dots with broader size distribution, broader bandwidth of emission an poorer quantum yield. (M.-C. Castanon et al. Materails Letters, 2005; 59: 529)

Cationic quantum dots are promising nanomaterials in big logical applications especially in gene delivery studies_ The most prominent cationic polymer is polyethyleneimine (PEI) for gene delivery. Polyethyleneimine (25 kDa branched) is accepted as gold standard in gene delivery applications because of high transfection efficiency. The polymer has been used to synthesize quantum dots to be used in biological applications. PEI coated CdS quantum dots were prepared with a broad (white-like) emission profile and quantum yields up to 60-70% at room temperature. However, these quantum dots emit in the visible region and have toxicity problem. Also most of the $Ag_2X$. (X:S, Se and Te)-NIRQDs in literature were synthesized by organic, preparation methods. Examples to such studies are given in the following references; Du Y., et al. JACS 2010; 132: 1470-1; Jiang P. et al., Chemistry of Materials 2011; 24:3-5; Sahu A. et al. JACS 2011; 133: 6509-12 and Yarema M. et al. ACS Nano. 2011; 5: 3758. Those quantum dots are emitting in the range of 700-1100 nm wavelength with very low quantum yields (up to 2%).

Recently, there are some reports on the synthesis of $Ag_2X$-NIRQDs in aqueous medium Acar et al., prepared 2-mercaptopropionic acid coated $Ag_2S$ NIRQDs emitting in the 780-950 nm range with quantum yields up to 17% which is improved up to 39% upon aging. These $Ag_2S$ NIRQDs have the highest quantum yield reported until now (J. Mater. Chem., 2012, 22, 14674). Yang et al. reported $Ag_2S$-BSA QDs synthesized in aqueous medium with emissions between 1050-1295 nm which is the second NIR range (Yan et al, *Nanotechnology,* 2013, 24, 055706). Glutathione stabilized $Ag_2S$ QDs were also prepared and reported with 0.96-1.97% quantum yield with emission between 960-1050 nm (Tan et al., *ACS Applied Materials & Interfaces,* 2013, 6, 18-23)

In a patent application WO 2012/163078 A1, a silver sulfide based quantum dot with a hydrophilic coating(s) is synthesized and claimed to have high fluorescence yield and stability, high biocompatibility and homogeneous size. And also a method of synthesizing this QD via a simple, easy to control, easy to implement route of synthesis is reported in this patent application. Although the synthesis method is claimed to be convenient, the defined method involves two step syntheses in which the first step produces organic soluble hydrophobic particles at 80-350° C. and the second step involves transfer of particles into aqueous phase through ligand exchange of the hydrophobic molecule with a hydrophilic one. As mentioned before, this method causes a shift of emission peak towards longer wavelengths and some broadening in the emission peak. Also, those particles have a crystal core size around 5 nm and luminesce around 1200 nm. This falls into second NIR window and expensive and low sensitivity InGaAs detector is required for the luminescence detector.

From this respect, it is apparent that there is no solution to all these obstacles in the prior art: the problems being appropriate emission window such as 700-900 nm, low quantum yields, cytotoxicity, transfection efficiency and mild conditions for the method of synthesis. In the literature there is no example to a method of synthesizing such quantum dot via an aqueous, one-step, low temperature route. Here, in this invention a novel cationic quantum dot which is capable of luminescence at the desired near-IR range at the wavelength of 700-900 nm with dramatically improved quantum yield and high transfection efficiency and low toxicity is claimed and also a method of synthesizing such quantum dot via a single step and aqueous reaction at low temperatures.

The technology behind this invention is the mixed coating of the quantum dots and the use of silver chalcogenide as nontoxic near-IR emitting quantum dot. With the mixed coating approach that is followed in this invention, a dense packing on the surface of the quantum dot is suggested therefore the problems related to defects that may exist resulting in non-radiative coupling events and low luminesce is eliminated. It had been demonstrated that mixed coating approach shows a synergistic effect on stabilization and reduction of the particle size. In the mixed coating approach, a small molecule preferentially a thiolated molecule and a macromolecule capable of binding to Silver-chalcogenide crystal surface was used as a coating material for the semiconductor crystal. Addition of small molecules next to polymeric coatings results in limiting the crystal growth and improvement of surface pasifization since they bind to surface strongly and more densely at sites left unpassified by the large polymeric coating. Therefore, mixed coatings are proved to produce smaller particles with better luminescence intensity compared to quantum dots coated only with polymeric coating. With this approach behind, aqueous cationic Near-IR emitting silver sulfide quantum dots (Cat-$Ag_2$S-QD) with maximum emission at around 800-850 nm with quantum yields up to 150% with respect to LDS (LDS 798 Near-IR laser dye, quantum yield is 14% was reported by the producer) are synthesized at room temperature in aqueous medium. This luminescence window is suitable for detection with sensitive and cheap Si detectors. High quantum yields are highly advantages for improved penetration/imaging depth and signal/noise ratio and more efficient than high concentration (Won et al, Molecular Imaging, Vol 11, No 4, pp 338-352, 2012). Cytotoxicity studies done on several quantum dots (Cat-$Ag_2$S-QDs) demonstrated the significant improvement of cytocompatibility as compared to 25 kDa polyethyleneimine which is accepted to be the gold standard for gene transfection. Also with the cell uptake studies it is demonstrated that the Cat-$Ag_2$S-QDs are internalized by cells and may be used as optical probes in optical imaging. Also, in vitro studies demonstrated that Cat-$Ag_2$S-QDs are capable of condensing and protecting GFP and the transfection efficiencies are enhanced as compared to PEI.

SUMMARY OF THE INVENTION

In one aspect, the present invention is directed to a novel near-IR emitting cationic quantum dot which is capable of luminescence at the desired near-IR range at the wavelength of 800-850 nm with improved quantum yield and high transfection efficiency and low toxicity. The quantum dot is a silver chalcogenide selected from a group comprising silver sulfide, silver selenide, silver telluride or a mixture with a mixed coating wherein the coating comprises of at least 2 different types of materials one being a macromolecule selected from a group of polymers comprising polyethyleneimine, poly(dimethylaminoethyl methacrylate), Poly(amido amine) (PAMAM), poly-L-lactic acid (PLLA), dendrimers with amine end groups such as PAMAM and chitosan and the other one is being a small molecule selected from a group comprising thiolates, carboxylates and amines.

In a second aspect, the invention is directed to a method of the single step synthesis of mixed coated silver chalcogenide quantum dots including the steps of
 d) Reacting water soluble silver salt and water soluble chalcogenide source in an aqueous medium in the presence of the coating materials at room temperature under inert atmosphere between pH 5.5-11 and
 e) Stirring the solution for crystal growth at room temperature
 f) Subsequently washing the resulting quantum dot with water The third aspect of the invention is directed to a novel near-IR emitting cationic quantum dot with a mixed coating which has improved cytocompatability, quantum yield and transfection efficiency and is synthesized via a single step, homogeneous reaction that takes place in aqueous solution at low temperatures.

And final aspect of the invention is the use of these silver chalcogenide quantum dots in sensors, quantum dot sensitized solar cells, fluorescent tagging and medical applications such as medical imaging including tumour detection and labelling, therapy including drug delivery and transfection.

DETAILED DESCRIPTION OF THE INVENTION

Figure 1:
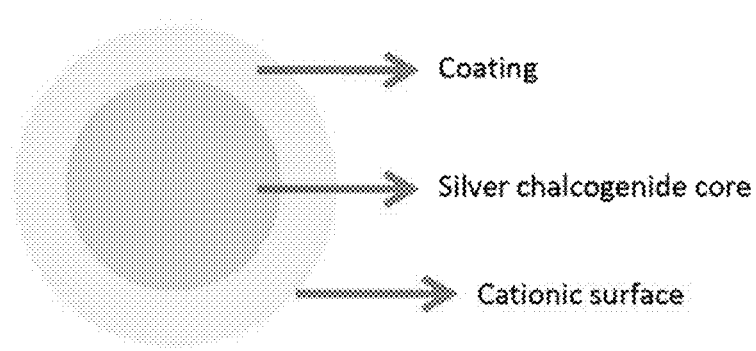
FIG. 1 The illustration of the cationic silver chalcogenide quantum dot with a binary coating.

One aspect of the invention is a near-IR emitting cationic silver chalcogenide quantum dot with a mixed coating wherein the silver chalcogenide is selected from a group comprising silver sulfide ($Ag_2S$), silver selenide ($Ag_2Se$) silver telluride ($Ag_2Te$) and mixtures thereof and the mixed coating comprises of at least two types of materials both are capable of binding to silver chalcogenide surface and one being a macromolecule selected from a group of polymers comprising polyethyleneimine, poly(dimethylaminoethyl methacrylate), Poly(amido amine)dendrimer (PAMAM), dendrimers with amine end groups and chitosan and the other one is being a small molecule selected from a group of small molecules comprising thiolases, carboxylates and amines. In a preferred embodiment of the invention, the silver chalcogenide is selected to be silver sulfide ($Ag_2S$). In another preferred embodiment of the invention, the macromolecular coating material is selected to be polyethyleneimine (PEI) and more preferably a 25 kDa branched PEI. In another preferred embodiment of the invention the small molecule coating is selected to be a water soluble thiolated small molecule and preferably a propionic acid and most preferably 2-mercaptopropionic acid.

A preferred embodiment of the invention is a near-IR emitting cationic silver chalcogenide quantum dot as described above wherein the silver chalcogenide is selected to be silver sulfide ($Ag_2S$) with the mixed coating comprising at least 2 types of materials one of which is selected to be polyethyleneimine and the other one is selected to be a thiotated small molecule and preferably is a propionic acid and most probably is 2-mercaptopropionic acid.

In a preferred embodiment of the invention, a near-IR emitting cationic silver chalcogenide quantum dot wherein the silver chalcogenide is selected to be silver sulfide ($Ag_2S$) with the mixed coating comprising at least 2 types of materials one of which is selected to be polyethyleneimine and the other one is selected to be a thiolated small molecule and preferably is a propionic acid and most preferably is 2-mercaptopropionic acid.

More preferred embodiment of this invention is related to a near-IR emitting cationic silver chalcogenide quantum dot as described above wherein the silver chalcogenide is selected to be silver sulfide ($Ag_2S$) one of the coating material is selected to be polyethyleneimine—preferably 25 kDa branched polyethyleneimine and the other coating material is selected to be 2-mercaptopropionic acid and the quantum dot is characterized as the molar ratio of polyethyleneimine (PEI) to 2-mercaptopropionic acid used in the synthesis is ranging between 60/40 to 80/20.

Another preferred embodiment of the invention is related to a near-IR emitting cationic silver chalcogenide quantum dot ($Cat-Ag_2X-QD$) as described above wherein the quantum dot is further characterized as the molar ratio of silver cation source to the total coating material used in the synthesis is 1/5.

Another preferred embodiment of the invention is a near-IR emitting cationic silver chalcogenide quantum dot ($Cat-Ag_2X-QD$) as described above wherein the quantum dot is fluffier characterized as the molar ratio of silver cation source to the sulfide source used in the synthesis is 4.

The most preferred embodiment of the invention is a near-IR emitting, cationic silver chalcogenide quantum dot ($Cat-Ag_2X-QD$) as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid and the quantum dot is characterized as:

iv. The molar ratio of polyethyleneimine (PEI) to 2-mercaptopropionic acid used in the synthesis is 80/20
v. The molar ratio of silver cation source to the total coating material used in the synthesis is 1/5 and
vi. The molar ratio of silver cation source to sulfide source used in the synthesis is 4

Another aspect of the invention is a method of synthesizing a near-IR emitting cationic silver chalcogenide quantum dot with a mixed coating wherein the silver chalcogenide is selected from a group comprising silver sulfide ($Ag_2S$), silver selenide ($Ag_2Se$), Silver Telluride ($Ag_2Te$) and mixtures thereof and the mixed coating comprises of at least 2 types of materials both are capable of binding to silver chalcogenide surface and one being a cationic macromolecule selected from a group of polymers comprising polyethyleneimine, poly(dimethylaminoethyl methacrylate), Poly(amido amine) (PAMAM), poly-L-lactic acid (PLLA), dendrimers with amine end groups and chitosan and the other one is being a small molecule selected from a group of small molecules comprising thiolates, carboxylates and amines and the method is characterized as a single-step, homogeneous, aqueous and the method taking place at room temperature.

Another selected embodiment of the invention is related to method of synthesizing a near-IR emitting cationic silver chalcogenide quantum dot as described above, comprising the steps of
iv. Reacting water soluble silver salt and water soluble chalcogenide source in an aqueous medium in the presence of the coating materials at room temperature, at a pH ranging from 5-11 under inert atmosphere and
v. Stirring the mixture for crystal growth and
vi Subsequently washing the resulting quantum dot with water A preferred embodiment of the invention is a method of synthesizing a near-IR emitting cationic silver chalcogenide quantum dot with a binary coating as described above wherein the silver chalcogenide is selected to be silver sulfide ($Ag_2S$).

Another preferred embodiment of the invention is related to a method of synthesizing a near-IR emitting cationic silver chalcogenide quantum dot with a binary coating wherein the coating materials are selected from at least two types of materials one of which is a cationic polymeric coating and another one is a selected from a group of small molecules with an affinity to silver chalcogenide crystal surface as described above. In a more preferred embodiment of the invention the polymeric coating is selected to be polyethyleneimine and the other coating is selected from a group of small molecules comprising thiolates, carboxylates and amines.

Another embodiment of the invention is the method of synthesizing the cationic silver chalcogenide quantum dot as described above wherein one of the coating material is a macromolecule selected from a group of polymers comprising polyethyleneimine, poly(dimethylaminoethyl methacrylate), Poly(amido amine) (PAMAM), poly-L-lactic acid (PLLA), dendrimers with amine end groups and chitosan and the other one is selected to be a thiolated small molecule and preferably is a propionic acid and most probably is 2-mercaptopropionic acid.

Another preferred embodiment of the present invention is the method of synthesizing the cationic silver chalcogenide quantum dot as described above wherein the silver chalcogenide is selected to be silver sulfide ($Ag_2S$) with the mixed coating comprising at least 2 types of materials one of which is selected to be polyethyleneimine and the other one is selected to be a thiolated small molecule and preferably is a propionic acid and most probably is 2-mercaptopropionic acid.

Another preferred embodiment of the invention is related to a method of synthesizing the cationic silver chalcogenide quantum dot as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid and the said method is characterized as the used polyethyleneimine (PEI) to 2-mercaptopropionic acid mole ratio of is selected to be in between 60/40 to 80/20.

Also another preferred embodiment of the invention is about a method of synthesizing the cationic silver chalcogenide quantum dot as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid and the method is characterized as the used silver cation source to the total coating material mole ratio is 1/5.

A specialized embodiment of the invention is about a method of synthesizing the cationic silver chalcogenide quantum dot as described above wherein the silver chalcogenide is selected to be silver sulfide ($Ag_2S$), one of the coating material is selected to he polyethyleneimine—preferably 25 kDa branched polyethyleneimine and the other coating material is selected to be 2-mercaptopropionic acid and the method is characterized as the used silver cation source to sulfide source mole ratio is 4.

A preferred embodiment of the invention is related to a method of synthesizing the cationic silver chalcogenide quantum dot as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid and the method is characterized as follows:

v. The molar ratio of used polyethyleneimine (PEI) to 2-mercaptopropionic acid is 80/20
    vi. Then molar ratio of silver cation source to the total coating materials is set to 1/5
    vii. The molar ratio of silver cation source to sulfide source is 4 and
    viii. The pH of the reaction mixture is set to a value between 5.5-11.0.

The third aspect of the invention is directed to a novel near-IR emitting cationic quantum dot with a mixed coating wherein the silver chalcogenide is selected from a group comprising silver sulfide ($Ag_2S$), silver selenide ($Ag_2Se$), Silver Telluride ($Ag_2Te$) and mixtures thereof and the mixed coating comprises of at least 2 types of materials both are capable of binding to silver chalcogenide surface and one being a macromolecule selected from a group of polymers comprising, polyethyleneimine, poly(dimethylaminoethyl methacrylate), Poly(amido amine) (PAMAM), poly-L-lactide acid (PLLA), dendrimers with amine end groups and chitosan and the other one is being a small molecule selected from a group of small molecules comprising thiolates, carboxylates and amine which has improved quantum yield and transfection efficiency and is synthesized via a single step, homogeneous reaction that takes place in aqueous solution at low temperatures and preferably comprising the steps of;

iv. Reacting water soluble silver salt and water soluble chalcogenide source in an aqueous medium in the presence of the coating materials at room temperature, at a pH ranging from 5-11 under inert atmosphere and
    v. Stirring the mixture and
    vi. Subsequently washing the resulting quantum dot with water In a preferred embodiment of the invention the near-IR emitting cationic silver chalcogenide quantum dot synthesized as described above is characterized that the silver chalcogenide is selected to be silver sulfide ($Ag_2S$).

Another preferred embodiment of the invention is the near-IR emitting cationic silver chalcogenide quantum dot synthesized as described above wherein one of the coating materials is selected to be polyethyleneimine and the other one is being a small molecule selected from a group of small molecules comprising thiolates, carboxylates and amines.

Another preferred embodiment of the invention is the near-IR emitting cationic silver chalcogenide quantum dot synthesized as described above wherein one of the coating material is a macromolecule selected from a group of polymers comprising polyethyleneimine, poly(dimethylaminoethyl methacrylate), Poly(amido amine) (PAMAM), poly-L-lactide acid (PLLA), dendrimers with amine end groups and chitosan and the other one is selected to be a thiolated small molecule and preferably at propionic acid and most probably is 2-mercaptopropionic acid.

Another embodiment of the invention is the near-IR emitting cationic silver chalcogenide quantum dot synthesized as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid.

Another preferred embodiment of the invention is a near-IR emitting cationic silver chalcogenide quantum dot as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid and the quantum dot wherein the quantum dot is characterized as the molar ratio of polyethyleneimine (PEI) to 2-mercaptopropionic acid used in the synthesis is ranging between 60/40 to 80/20.

Another embodiment of the invention is the near-IR emitting cationic silver chalcogenide quantum dot as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid wherein the quantum dot is further characterized as the molar ratio of silver cation source to the total coating material used in the synthesis is 1/5.

Another embodiment of the invention is near-IR emitting cationic silver chalcogenide quantum dot as described above wherein the silver chalcogenide is selected to be silver sulfide ($Ag_2S$), one of the coating material is selected to be polyethyleneimine—preferably 25 kDa branched polyethyleneimine and the other coating material is selected to be 2-mercaptopropionic acid and the quantum dot is further characterized as the molar ratio of silver cation source to the sulfide source used in the synthesis is 4. Another embodiment of the invention is the near-IR emitting cationic silver chalcogenide quantum dot as described above wherein the silver chalcogenide is selected to be silver sulfide ($Ag_2S$), one of the coating material is selected to be polyethyleneimine preferably 25 kDa branched polyethyleneimine and the other coating, material is selected to be 2-mercaptopropionic acid and the quantum dot is characterized as:
  v. The molar ratio of polyethyleneimine (PEI) to 2-mercaptopropionic acid used in the synthesis is 80/20
  vi. The molar ratio of silver cation source to the total coating material used in the synthesis is 1/5 and
  vii. The molar ratio of silver cation source to sulfide source used in the synthesis is 4.
  viii. The pH of the reaction mixture is set to a value between 5.5-11.0

One final aspect of the invention is the use of the near-IR emitting cationic silver chalcogenide quantum dot with a mixed coating wherein the coating comprises of at least 2 different types of materials as described earlier in sensors, quantum dot sensitized solar cells, fluorescent tagging and medical applications such as medical imaging including tumor detection and labeling, therapy including drug delivery and transfection.

The near-IR emitting cationic silver chalcogenide quantum dot can especially be used as optical probes, transfection agents and specific disease targeting agents.

Quantum Dots have great potential in the field of biotechnology and medicine. Broad absorption and narrow emission profiles of quantum dots allow excitation of different quantum dots at a single wavelength but emission from different quantum dots at different wavelengths depending on the crystal size of the QD. This property of QDs is very advantageous for labeling; including peptides, oligonucleotides, cells, tissues and as such. Fluorescent labeling also known as fluorescent tagging is defined as a fluorophore usually an organic molecule—is being chemically attached to a biomolecule in order for the detection of the said protein, antibody, oligonucleotide, amino acid, etc. Long luminescence lifetime of quantum dots with respect to organic fluorophores, simultaneous excitation of quantum dots emitting at different wavelengths at a single excitation wavelength, higher extinction coefficient make quantum dots good fluorescent tag candidates. Considering the NIR region, lack of organic fluorophores makes NIR quantum dots very attractive for fluorescent tagging, These also provide valuable means for optical imaging for tracking and diagnosis. Considering this quantum dot's ability to cross cell membrane is a critical spec for cell labeling and imaging applications. "Medical imaging" is another application area that quantum dots stated in the current invention can be useful for. Medical imaging is a method of creating images of the human body for diagnostic purposes mostly. "Tumor detection" is a branch of medical imaging that quantum dots can be used for. Quantum dots can also be used for therapeutic purposes and preferably as disease specific drug delivery vehicles. Small drugs such as chemotherapeutic drugs and/or oligonucleotides can be conjugated to quantum dots. Gene delivery application can also be conducted by the cationic quantum dots which is a process of foreign DNA, siRNA, mRNA introduction to host cells and done for mostly gene therapy and genetic modifications. Quantum dots conjugated with drugs are valuable thermostatic materials where conjugation with disease or tissue specific ligands such as molecules, antibodies, peptides, proteins provide site/tissue/disease specific delivery of QDs and hence the therapeutic agent. Fluorescence of thermostatic QDs also provide opportunity to monitor the influence of delivered therapeutic agent to the target site with optical imaging. Optical probes as used in this invention can be defined as the chemical tracking devices.

Quantum Dots can be utilized as optical probes in variety of sensors detecting a chemical, an ion or a process where interaction of quantum dots with the target species enhances or reduces the luminescence of the quantum dot. Broad absorbance range of quantum dots is also useful in quantum dot sensitized solar cell applications. NIR quantum dots have strong absorbance in the visible region which allows enhanced utilization of the solar energy with NIR quantum dots compared to those which absorb the UV and emit in the visible range, such as cadmium chalcogenides. NIR emitting quantum dots as described herein can be used as optical probes for sensors and as sensitizers in solar cells.

DEFINITIONS

Quantum dots as used herein this invention refer to luminescent nanocrystals that are made of semiconductor materials and exhibits quantum confinement effect. Cationic quantum dots refer to quantum dots that have cationic outer surfaces in other words coated with organic materials with cationic nature. Cationic materials refer to cationic polymers in this invention. Cationic polymers that can be used as a coating for cationic quantum dots can he listed as follows: polyethyleneimine, poly (dimethylaminoethyl methacrylate), Poly(amido amine) (PAMAM), poly-L-lactide acid (PLLA) dendrimers with amine end groups and chitosan. An example to the polymers used in this invention is polyethyleneimine (PEI). PEI may be in a linear or branched form; and the molecular weights may range from 1,800-70,000 Da.

Mixed coating as used herein refers to "binary coating" and differs from double coating and the resulting quantum dot differs from a core/shell type quantum dots. The coating materials used in this invention can he classified under 2 groups one of which is a "cationic polymer" also referred as "macromolecule" or "macromolecular coating" can be defined as large molecules that are created by polymerization of smaller subunits and the ones that are used in this invention are listed above.

The other coating material is selected from a group comprising water soluble small molecules with ability to bind silver chalcogenide crystal surface such as thiolates, amines and carboxylates. Small molecules as used here in this invention refer to low molecular weight organic compounds. Examples to these water soluble small molecules suitable for use in the present invention include but not limited to thioglycolic acid, 3-mercaptopropionic acid, 2-mercaptopropionic acid, thioglycerol, glutathione and cystamine.

Silver chalcogenide mixture as used herein refers to $Ag_2S$, $Ag_2Se$, and $Ag_2Te$ mixture in alloy form or as physical mixture. Silver chalcogenide mixture may also refer to core/shell type structures comprising of but not limited to silver chalcogenides such as, $Ag_2Se/Ag_2S$; $Ag_2Te/Ag_2Te/Ag_2Se$; $Ag_2Te/Ag_2S$, $Ag_2S/CdS$, $Ag_2S/AgInS$, $AgS/CdS/ZnS$.

In this detailed description of the invention, some exemplary references are used for illustrative purposes only therefore it should be understood that the invention is not limited to the scope of these particular embodiments. The terminology used herein is for the purpose of description and not to limit the scope of the invention.

Transfection as used herein this invention refers to a process in which nucleic acids are delivered into a cell.

General Synthesis Method

All reactions were performed under an inert atmosphere. Typically, a water soluble silver salt and 0.25 equimolar of chalcogenide source is dissolved separately in deoxygenated water. Desired amounts of the coating materials (mixed coating) are added to the silver solution and pH of the solution was adjusted to desired value using NaOH and CH$_3$COOH solutions. Chalcogenide solution was added to the silver and coating mixture under vigorous mechanical stirring at 5000 rpm at room temperature (25° C.). During the reaction, samples were taken at different time zones to follow the particle growth. Prepared quantum dot solutions were washed with deionized water using Amicon-Ultra centrifugal filters (30000 Da cut off) and stored in dark at 4° C. Examples of water soluble silver salts suitable for use in the present invention include, but not limited to silver nitrate, silver acetate, silver propionate, silver sulfate, silver butyrate, silver isobutyrate, silver benzoate, silver tartrate silver salicylate, silver malonate, silver succinate and silver lactate. Examples of chalcogenide sources suitable for use in the present invention include, but not limited to sodium sulfide (Na$_2$S); Sodium Selenide (Na$_2$Se); Sodium Telluride (Na$_2$Te); hydrogen sulfide (H$_2$S); hydrogen selenide (H$_2$Se); Hydrogen Telluride (H$_2$Te); thioacetamide; thioureas; sodium hydrogen telluride (NaHTe); Sodium hydrogen selenide (NaHSe).

General Characterization Methods

Absorbance spectra of the prepared silver chalcogenide quantum dots were recorded in the 300-1100 nm range and crystal size of QDs were calculated from the absorption onset determined from the absorbance spectrum using Brus equation (eqn. 1):

$$\Delta E = \frac{\hbar^2 \pi^2}{8R^2}\left[\frac{1}{m_e}+\frac{1}{m_h}\right]-1.8\frac{e^2}{\varepsilon_{Ag_2S} 4\pi\varepsilon_0 R} \quad (1)$$

Wherein R is the radius of the nanocrystal, m$_c$ (0.286 m0) and m$_h$ (1.096) are the respective effective electron and hole masses for inorganic core, and $\varepsilon_{Ag_2S}$ (5.95) is the dielectric constant and $\Delta E$ is the band gap energy difference between the bulk semiconductor and the nanocrystal.

Fluoresence spectra of QDs were recorded on a homemade device equipped with an amplified silicon detector sensitive over the wavelength range of 400-1100 nm together with a lock-in amplifier. A continuous-wave, frequency-doubled Nd:vanadate laser was used to excite samples at 532 nm. A concave gold reflector and a 0.5-meter Czerny-Turner monochromator was used to collect and image emission. A long-pass filter with a transmission of 90% between 550-1100 nm was used. Data corrected with the spectral response of the detection system.

Quantum yield of QDs were calculated according to the formula provided below: s=r(Is/Ir) (An/As)(ns/nr), where s, Is, As and ns are the QY, emission peak area, integrated absorption intensity and refractive index of QDs, respectively, and r, Ir. Ar and nr are the corresponding parameters of LDS 798 MR dye in methanol (quantum yield reported as 14% by the producer). For QY calculations five different solutions of QD and reference dye were prepared at five different concentrations.

TEM analysis of nanoparticles was performed using a EWE, JEM-ARM200CFEG UHR-Transmission Electron Microscope (JEOL, Japan). Hydrodynamic size and zeta potential of the aqueous nanoparticles were measured with a Malvern Zetasizer Nano-ZS.

Quantum Dots were digested with 65% nitric acid—96% sulphuric acid mixture and diluted to certain volumes. Ag$^+$ ion concentrations in solutions were measured by ICP-OES and calculated using a standard curve of known Ag$^+$ ion concentrations.

In Vitro Tests

HeLa cell lines were cultured in Dulbecco's Modified Eagle Medium (DMEM) supplemented with 10% (v/v) fetal bovine serum and antibiotics (Penicillin/Streptomycin) in a 5% CO$_2$-humidified incubator at 37° C.

50000 HeLa cells were cultured in dishes and incubated for 18 h. After incubation, culture medium was replenished and cells were incubated with Quantum Dot solution with 2.5 µg/mL Ag$^+$ ion concentration for 6 hours. Cells were washed with PBS (pH 7.2) and fixed with 4% para-formaldehyde for 15 minutes. A home-niade confocal microscope system equipped with a 60× (NA: 1.49) oil immersion objective and a Si detector was used to image QD internalization by the cells. Briefly, cells were placed on the stage of the confocal laser scanning microscope and exited at 532 nm by laser.

EXAMPLES

The following examples are provided to illustrate the present invention and are not intended to limit the scope of the invention. Table 1 lists reaction parameters for the synthesis of PEI coated Ag$_2$S QD, 2MPA coated Ag$_2$S QD, cationic Ag$_2$S QDs with mixed coating at pH 10 and properties of the resulting Ag$_2$S QDs. Table 2 lists properties of cationic silver sulfide quantum dots at different pH values.

Example 1

Figure 2:
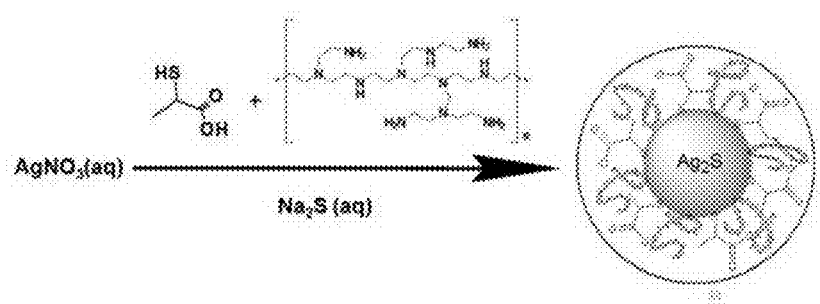
FIG. 2 Aqueous synthesis of PEI and 2-MPA coated $Ag_2$S NIRQDs.

General Synthesis Method and particle characterization of polyethyleneimine (PEI)/2-mercaptopropionic acid coated Silver Sulfide (Ag$_2$S) (Cat-Ag$_2$S-QD) nanoparticles (as shown in FIG. 2)

All reactions were performed wider an inert atmosphere. Typically, PEI and 2-MPA were added to an aqueous solution of AgNO$_3$ (0.25 mmol in 75 mL deoxygenated MilliQ water) and pH of the solution was adjusted to desired value using NaOH and CH$_3$COOH solutions (2.5 M). Na$_2$S (0.0625 mmol in 25 ml of deoxygenated water) solution was added to the PEI/2MPA/AgNO$_3$ solution under vigorous mechanical stirring at room temperature (25° C.) (Scheme 1.) Samples were withdrawn from the reaction mixture for the assessment of particle growth via UV-Vis spectrophotometer and spectrofluorometer. Usually, crystal growth stops in 5 min, therefore, all comparative reactions were quenched in liquid nitrogen (after 5 minute crystal growth, washed with deionized water using Amicon-Ultra centrifugal filters (30000 Da cut off and stored in dark at 4° C.

Figure 3:
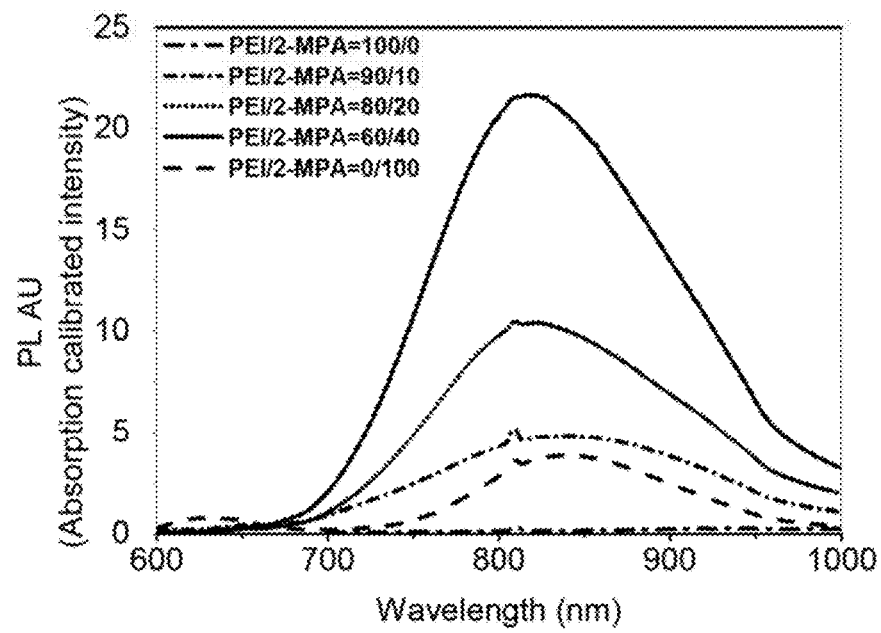
FIG. 3 Photoluminescence spectra of Cat-$Ag_2$S-QDs prepared with different PEI/2MPA ratios (mole of Ag:mole of S=4, Reaction at room temperature and pH 10, reaction time: 5 min).

The prepared Cat-Ag$_2$S-QDs have PEI and 2-MPA as coating material on the surface. The ratio between the PEI and 2-MPA was studied to obtain stable nanoparticles with high quantum efficiency. PEI to 2-MPA ratio was changed as 100/0, 90/10, 80/20, 60/40, 0/100 (Table 1). FIG. 3 is the normalized absorbance graph of the prepared Cat-Ag$_2$S-QDs. As depicted from the figure, the best PEI/2-MPA ratios are 60/40 and 80/20.

Figure 4:
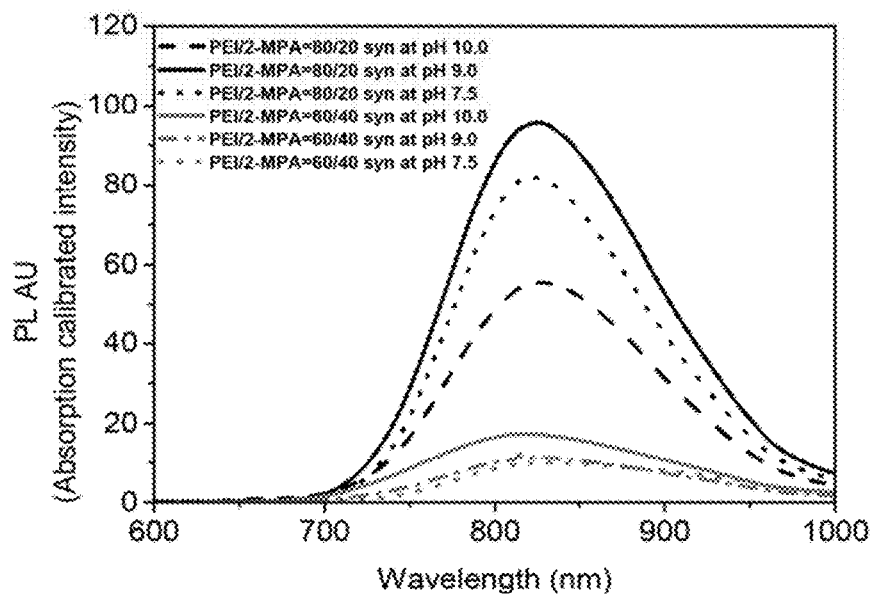
FIG. 4 Photoluminescence spectra of Cat-$Ag_2$S-QDs prepared with PEI/2MPA ratios of 60/40 and 80/20 at pH 7.5, 9 and 10 (Mole of Ag:mole of S=4, mole of: mole of PEI=3:1 mole of Ag:mole of 2-MPA=2; Reaction at room temperature, reaction time: 5 min).

At the 60/40 and 80/20 PEI/2-MPA ratios reactions were carried out also pH 5.5, 7.5, 9 and 11. Best luminescence was obtained at pH 10 with 60/40 PEI/2MPA composition and pH 9 for 80/20 PEI/2MPA (FIG. 4). In addition, emission peaks with 60/40 PEI/2MPA of Cat-Ag$_2$S-QDs has two emission maximum and have poor colloidal stability at pH values below 9. However, Cat-Ag$_2$S-QDs with 80/20 PEI/2MPA is stable and have strong emission.

Properties of Cat-Ag$_2$S-QDs with binary coating as described herein influenced by the pH of the medium, as well. Table 2 shows the changes in particle properties of Cat-Ag$_2$S-QDs synthesized with PEI/2M PA ratio of 80/20 at pH9 and at room temperature with the pH after synthesis and purification. At pH 7.4 quantum yield is doubled compared to pH 9 and reached to 166% at pH 5.5.

Figure 5:
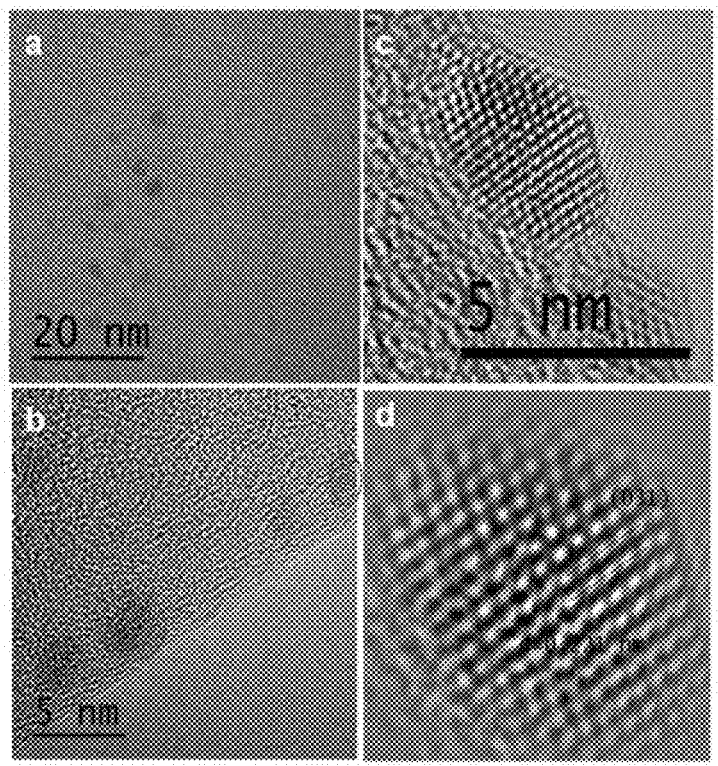
FIG. 5 TEM images of Cat-$Ag_2$S-QDs with 80/20 PEI/2MPA synthesized at pH 9.0 particle distributions a) 20 nm and b 5 nm scale c) diffraction of $Ag_2$S crystal lattice d) d-spacing between a plane determined by a focused image.

TEM images of the particles reveal mostly spherical particles with sizes around 2-4 nm (FIG. 5).

TABLE 1

Effect of PEI/2-MPA ratios on the properties of Cat-Ag$_2$S-QDs

| PEI (%) | 2-MPA (%) | Reaction pH | $\lambda_{abs(cutoff)}$[a] (nm) | Size[b] (nm) | Band gap (eV) | $\lambda_{em\ (max)}$ (nm) | FWHM, nm | Dh[c] (nm) | Zeta pot. (mV) |
|---|---|---|---|---|---|---|---|---|---|
| 100 | 0 | 10 | 906 | 2.94 | 1.37 | — | — | 4.0 | 51 |
| 90 | 10 | 10 | 674 | 2.23 | 1.48 | 838 | 175 | 2.9 | 34 |
| 80 | 20 | 10 | 761 | 2.48 | 1.63 | 819 | 173 | 3.5 | 28 |
| 60 | 40 | 10 | 777 | 2.52 | 1.60 | 817 | 168 | 3.8 | 36 |
| 0 | 100 | 7.5 | 806 | 2.61 | 1.54 | 837 | 128 | 7.10 | −62 |

[a]Absorbance onset.
[b]Calculated by Brus equation.
[c]Hydrodynamic diameter measured by DLS at pH 7.4 and reported as the number average.

TABLE 2

Influence of pH on the properties of Ag$_2$S-PEI/2MPA Cat-Ag$_2$S-QDs*

| pH | $\lambda_{abs(cutoff)}$[a] (nm) | Size[b] (nm) | Band gap (eV) | $\lambda_{em\ (max)}$ (nm) | FWHM, nm | Dh[c] (nm) | Zeta pot. (mV) | QY (%) |
|---|---|---|---|---|---|---|---|---|
| 5.5 | 783 | 2.54 | 1.59 | 812 | 151 | 9.4 | 63 | 166 |
| 7.4 | 783 | 2.54 | 1.59 | 828 | 150 | 8.9 | 60 | 150 |
| 9.0 | 783 | 2.54 | 1.59 | 825 | 170 | 8.0 | 32 | 77 |

[a]Absorbance onset,
[b]Calculated by Brus equation.
[c]Hydrodynamic diameter measured by DLS and reported as the number average.
[d]Quantum yield calculated with respect to LDS 798 near-IR dye (Ag:S = 4, Ag:PEI = 1:4, Ag:2-MPA = 1:1, Temp = RT, reaction pH = 9, 5 min reaction).
*Cationic Ag$_2$S quantum dots synthesized with 80% PEI, 20% 2-MPA at pH 9.0 were used.

Example 2

Synthesis method of polyethyleneimine (PEI)/2-mercaptopropionic acid coated silver sulfide (Ag$_2$S) nanoparticle with 60/40 molar ratio of PEI/2-mercaptopropionic acid. 2.14×10$^{-3}$ mmol PEI (0.75 mmol —NH$_2$) and 0.5 mmol 2-MPA (0.5 mmol —SH) were added to an aqueous solution of AgNO$_3$ (0.25 mmol in 75 mL deoxygenated MilliQ water) and pH of the solution was adjusted to 10. Na$_2$S (0.0625 mmol in 25 ml of deoxygenated water) solution was added to the PEI/2MPA/AgNO$_3$ solution under vigorous mechanical stirring at room temperature (25° C.) (Samples withdrawn from the reaction mixture for the assessment of particle growth via UV-Vis spectrophotometer and spectrofluorometer.) QDs washed with deionized water using Amicon-Ultra centrifugal filters (30000 Da cut off) and stored in dark at 4° C.

Example 3

Synthesis method of polyethyleneimine (PEI)/2-mercaptopropionic acid coated silver sulfide (Ag$_2$S) nanoparticle with 80/20 molar ratio of PEI/2-mercaptopropionic acid: 2.856'1.0$^{-3}$ mmol PEI (1 mmol —NH$_2$) and 0.25 mmol 2-MPA (0.25 mmol —SH) were added to an aqueous solution of AgNO$_3$ (0.25 mmol in 75 mL deoxygenated MilliQ water) and pH of the solution was adjusted to 9. Na$_2$S (0.0625 mmol in 25 ml of deoxygenated water) solution was added to the PEI/2MPA/AgNO$_3$ solution under vigorous mechanical stirring at room temperature (25° C.) (Samples withdrawn from the reaction mixture for the assessment of particle growth via Uv-vis spectrophotometer and spectrofluorometer.) QDs washed with deionized water using Amicon-Ultra centrifugal filters (30000 Da cut off) and stored in dark at 4° C.

Example 4

In Vitro cell internalization studies for polyethyleneimine (PEI)/2-mercaptopropionic acid coated Silver Sulfide (Ag$_2$S) nanoparticles.

Figure 6:
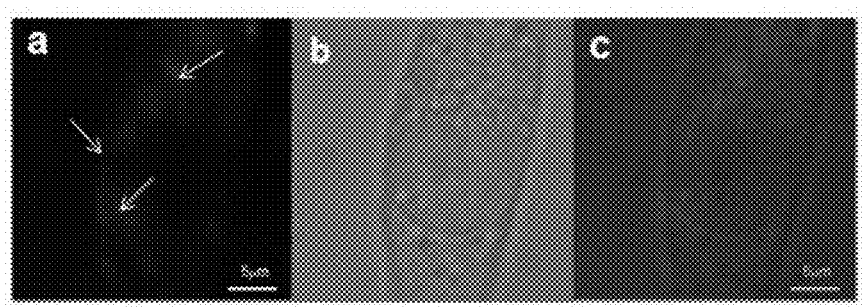
FIG. 6 Confocal images of HeLa cells treated with Cat-$Ag_2$S-QDs, Near IR (a), transmission (b) merged image (c) of an individual cell. Red color shows the quantum dots. Arrows show QDs in the cell.

Ag$_2$S quantum dots synthesized with 80/20 molar ratio of PEA/2M PA as described in example 3 was used for in vitro cell internalization and optical imaging of QDs in cells. Briefly, 50000 HeLa cells were cultured in dishes and incubated for 18 h. After incubation, culture medium was replenished and cells were incubated with Quantum Dot solution with 2.5 µg/mL Ag$^+$ ion concentration for 6 hours. Cells were washed with PBS (pH 7.2) and fixed with 4% para-formaldehyde for 15 minutes. A home-made confocal microscope system equipped with a 60× (NA: 1.49) oil immersion objective and a Si detector was used to image QD internalization by the cells. Briefly, both QD treated and untreated cells were placed on the stage of the confocal laser scanning microscope and exited at 532 nm by laser. A significant emission was detected from cells treated with QDs however, no emission, no autofluoresence was detected from the untreated cells in the equal scale of emission intensity. The study proves the efficient uptake of QDs and effectiveness of the NIR emission at in the NIR in cell imaging with no complication of autofluoresence from cells (FIG. 6).

Example 5

Cytotoxicity tests for polyethyleneimine (PEI)/2-mercaptopropionic acid coated Silver Sulfide (Ag$_2$S) nanoparticles For the cytotoxicity assessment HeLa cells were cultured in the 96-well plates in complete medium at 37° C. and 5% for 24 h. On the second day, medium was renewed and Qunatum Dots were added to the culture medium at 1-25 µg Ag$^+$/mL concentrations and incubated for another 24 h. On the third day, cells were washed with PBS. MTT (thiazolyl blue tetrazolium bromide (3-(4,5-dimethyl-thiazol-2yl)-2,5-diphenyltetrazolium bromide) solution was added on the cells and incubated for 4 h. Purple formazan was dissolved with DMSO:Ethanol (1:1) by gentle shaking for 15 min.

Figure 7:
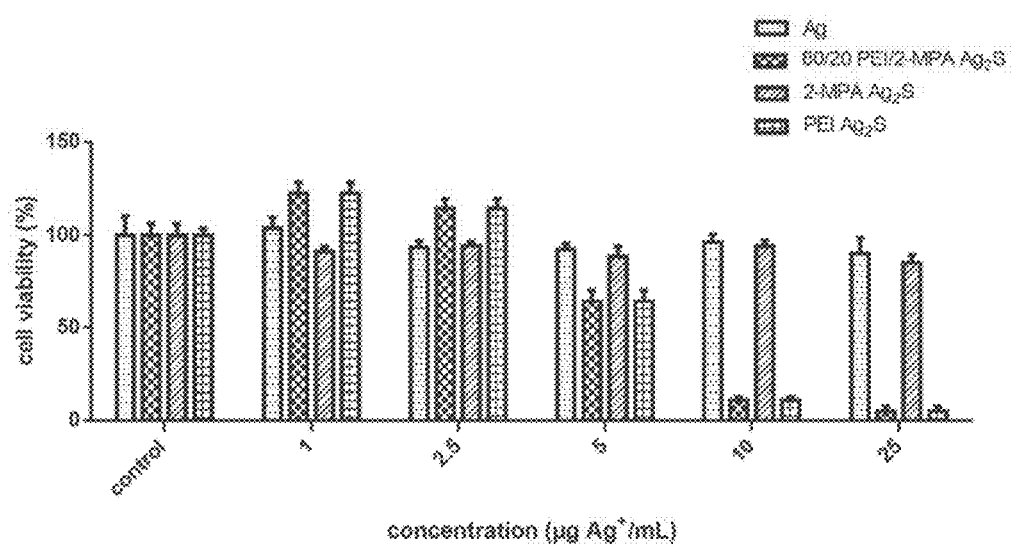
FIG. 7 MITT assays illustrating the percentage cell viability of HeLa cells exposed free $Ag^+$ Cat-$Ag_2$S-QD with 80/20 PEI/2MPA synthesized at pH 9, 2-MPA coated $Ag_2$S and PEI coated $Ag_2$S. Concentrations are based on $Ag^+$ ion concentration in QD solutions. This concentration range corresponds to 4.6-115 μg QD/mL.

Absorbance of formazan was measured at 600 nm with a reference at 630 nm on a microplate reader. Qunatum Dot absorbance in complete medium was measured as well and subtracted from MTT solution for the correction. Cytocompatibility of 100% polyethyleneimine coated, 100% 2-mercaptopropionic acid coated and 80/20 PEI/2MPA coated $Ag_2S$ Qunatum Dots were tested on HeLa cells at 1-25 μg $Ag^+$/mL concentrations (FIG. 7). The toxicity of free $Ag^+$ ion and PEI were also measured for comparison. At this concentration range free $Ag^+$ does not cause any significant cell death which is advantageous as compared to Cadmium; Mercury and Lead. The results can be summarized as follows: 100% 2MPA coated $Ag_2S$ QDs are not toxic; polyethyleneimine is highly toxic even at 2.8 μg/mL PEI level; but polyethyleneimine cytotoxicity diminishes dramatically as it binds to $Ag_2S$ surface; both $Ag_2S$ with 100% PEA and 80/20 PEI/2MPA showed no significant drop in the cell viability.

The invention claimed is:

1. A near-IR emitting silver chalcogenide quantum dot with a mixed coating, wherein the silver chalcogenide comprises a silver cation source and a sulfide source, wherein the silver chalcogenide is cationic, wherein the silver chalcogenide is one or more selected from a group consisting of silver sulfide, silver selenide, and silver telluride; wherein the mixed coating comprises at least two types of coating materials, wherein both of the coating materials bind to a silver chalcogenide surface, and the first type of the coating material is a macromolecule selected from the group of polymers consisting of polyethyleneimine, poly dimethylaminoethyl methacrylate, poly amido amine dendrimer, dendrimers with amine end groups and chitosan, and the second type of the coating material is selected from the group consisting of thiolates, carboxylates and amines.

2. The near-IR emitting silver chalcogenide quantum dot with the mixed coating of claim 1, wherein the silver chalcogenide is silver sulfide.

3. The near-IR emitting silver chalcogenide quantum dot with the mixed coating of claim 1, wherein the first type of the coating material is polyethyleneimine.

4. The near-IR emitting silver chalcogenide quantum dot with the mixed coating of claim 1, wherein the second type of the coating material is 2-mercaptopropionic acid.

5. The near-IR emitting silver chalcogenide quantum dot with the mixed coating of claim 1, wherein the silver chalcogenide is silver sulfide, the first type of the coating material is polyethyleneimine, and the second type of the coating material is 2-mercaptopropionic acid.

6. The near-IR emitting silver chalcogenide quantum dot with the mixed coating of claim 5, wherein the first type of the coating material is a 25 kDa branched polyethyleneimine, and a molar ratio of the polyethyleneimine to the 2-mercaptopropionic acid used in a synthesis ranges from 60/40 to 80/20.

7. The near-IR emitting silver chalcogenide quantum dot with the mixed coating of claim 1, wherein a molar ratio of the silver cation source to the coating material used is 1/5.

8. The near-IR emitting silver chalcogenide quantum dot with the mixed coating of claim 1, wherein a molar ratio of the silver cation source to the sulfide source used is 4.

9. The near-IR emitting silver chalcogenide quantum dot with the mixed coating of claim 8, wherein a molar ratio of the polyethyleneimine to 2-mercaptopropionic acid used in the synthesis is 80/20.

10. A method of synthesizing a near-IR emitting silver chalcogenide quantum dot with a mixed coating, wherein the silver chalcogenide comprises a silver cation source and a sulfide source, wherein the silver chalcogenide is one or more selected from a group consisting of silver sulfide, silver selenide, and silver telluride; wherein the mixed coating comprises at least two types of coating materials, wherein both of the coating materials bind to a silver chalcogenide surface, and the first type of the coating material is a macromolecule selected from the group of polymers consisting of polyethyleneimine, poly dimethylaminoethyl methacrylate, poly amido amine dendrimers, dendrimers with amine end groups and chitosan, and the second type of the coating material is selected from the group consisting of thiolates, carboxylates and amines, and
wherein the method is a single-step, homogeneous, aqueous, and takes place at room temperature.

11. The method of synthesizing the near-IR emitting silver chalcogenide quantum dot with the mixed coating of claim 10, comprising:
  i. reacting water soluble silver salt and a water soluble chalcogenide source in an aqueous medium in the presence of coating materials at room temperature, at a pH value ranging from 5 to 11 under an inert atmosphere to obtain a mixture;
  ii. stirring the mixture for a crystal growth; and
  iii. subsequently washing a resulting quantum dot with water.

12. The method of synthesizing the near-IR emitting silver chalcogenide quantum dot with the mixed coating of claim 10, wherein the silver chalcogenide is silver sulfide.

13. The method of synthesizing the near-IR emitting silver chalcogenide quantum dot with the mixed coating of claim 10, wherein the first type of the coating material is polyethyleneimine.

14. The method of synthesizing the near-IR emitting silver chalcogenide quantum dot with the mixed coating of claim 10, wherein the second type of the coating material is 2-mercaptopropionic acid.

15. The method of synthesizing the near-IR emitting silver chalcogenide quantum dot with the mixed coating of claim 10, wherein the silver chalcogenide is silver sulfide, the first type of the coating material is polyethyleneimine, and the second type of the coating material is 2-mercaptopropionic acid.

16. The method of synthesizing the near-IR emitting silver chalcogenide quantum dot with the mixed coating of claim 10, wherein the first type of the coating material is a 25 kDa branched polyethyleneimine, and a mole ratio of used polyethyleneimine to the 2-mercaptopropionic acid is from 60/40 to 80/20.

17. The method of synthesizing the near-IR emitting silver chalcogenide quantum dot with the mixed coating of claim 10, wherein a mole ratio of the silver cation source to the coating material is 1/5.

18. The method of synthesizing the near-IR emitting silver chalcogenide quantum dot with the mixed coating of claim 10, wherein a mole ratio of the silver cation source to the sulfide source is 4.

19. The method of synthesizing the near-IR emitting silver chalcogenide quantum dot with the mixed coating of claim 10, wherein a molar ratio of the polyethyleneimine to 2-mercaptopropionic acid is 80/20, wherein a pH value of a reaction mixture is set to a value of 5.5-11.0.

20. A near-IR emitting silver chalcogenide quantum dot with a mixed coating, wherein the silver chalcogenide is one or more selected from the group consisting of silver sulfide, silver selenide, and silver telluride; wherein the silver chalcogenide is cationic; wherein the mixed coating comprises at least two types of coating materials, wherein both of the coating materials bind to silver chalcogenide surface, and the first type of the coating material is a macromolecule selected from the group of polymers consisting of polyethyleneimine, poly dimethylaminoethyl methacrylate, poly amido amine dendrimers, dendrimers with amine end groups and chitosan, and the second type of the coating material is selected from the group consisting of thiolates, carboxylates and amines, wherein the near-IR emitting silver chalcogenide quantum dot is produced by a method of single-step, homogeneous, aqueous and takes place at room temperature.

21. The near-IR emitting silver chalcogenide quantum dot with the mixed coating of claim 20, wherein the method comprises the following steps:
  i. reacting water soluble silver salt and a water soluble chalcogenide source in an aqueous medium in the presence of coating materials at room temperature, at a pH value ranging from 5 to 11 under an inert atmosphere to obtain a mixture,
  ii. stirring the mixture; and
  iii. subsequently washing a resulting quantum dot with water.

22. The near-IR emitting silver chalcogenide quantum dot with the mixed coating of claim 20, wherein the silver chalcogenide is silver sulfide.

23. The near-IR emitting silver chalcogenide quantum dot with the mixed coating of claim 20, wherein the first type of the coating material is polyethyleneimine.

24. The near-IR emitting silver chalcogenide quantum dot with the mixed coating of claim 20, wherein the second type of the coating material is 2-mercaptopropionic acid.

25. The near-IR emitting silver chalcogenide quantum dot with the mixed coating of claim 20, wherein the silver chalcogenide is silver sulfide, the first type of the coating material is polyethyleneimine, and the second type of the coating material is 2-mercaptopropionic acid.

26. The near-IR emitting silver chalcogenide quantum dot with the mixed coating of claim 20, wherein the first type of the coating material is a 25 kDa branched polyethyleneimine, and a molar ratio of the polyethyleneimine to the 2-mercaptopropionic acid used is ranging from 60/40 to 80/20.

27. The near-IR emitting silver chalcogenide quantum dot with the mixed coating of claim 20, wherein a molar ratio of the silver cation source to the coating material used is 1/5.

28. The near-IR emitting silver chalcogenide quantum dot with the mixed coating of claim 20, wherein a molar ratio of the silver cation source to the sulfide source used is 4.

29. The near-IR emitting silver chalcogenide quantum dot with the mixed coating of claim 20, wherein a molar ratio of the polyethyleneimine to 2-mercaptopropionic acid used in the synthesis is 80/20, wherein the pH value of a reaction mixture is set to a value of 5.5-11.0.

* * * * *